(12) United States Patent
Poveda Estepa

(10) Patent No.: US 8,721,602 B2
(45) Date of Patent: May 13, 2014

(54) MEDICINAL BIOSECURITY AUTO DISPOSABLE SYRINGE

(76) Inventor: Luis Enrique Poveda Estepa, Madrid (ES)

( * ) Notice: Subject to any disclaimer, the term of this patent is extended or adjusted under 35 U.S.C. 154(b) by 0 days.

(21) Appl. No.: 13/390,201

(22) PCT Filed: Jun. 16, 2010

(86) PCT No.: PCT/ES2010/070401
§ 371 (c)(1),
(2), (4) Date: Mar. 27, 2012

(87) PCT Pub. No.: WO2011/018539
PCT Pub. Date: Feb. 17, 2011

(65) Prior Publication Data
US 2012/0179098 A1    Jul. 12, 2012

(30) Foreign Application Priority Data

Aug. 13, 2009  (ES) ............................... 200930368 U

(51) Int. Cl.
*A61M 5/00*  (2006.01)
(52) U.S. Cl.
USPC ......................................... 604/218; 604/110
(58) Field of Classification Search
USPC ......... 604/110, 218, 221–222, 225, 228–229, 604/231, 232, 139, 148, 153
See application file for complete search history.

(56) References Cited

U.S. PATENT DOCUMENTS

| 1,546,491 | A | * | 7/1925 | Kasmauskas | ................. | 604/206 |
|---|---|---|---|---|---|---|
| 2,789,559 | A | * | 4/1957 | Breitenbach | ................. | 604/228 |
| 3,902,491 | A | * | 9/1975 | Lajus | ............................ | 604/221 |
| 4,031,889 | A | * | 6/1977 | Pike | ............................ | 604/144 |
| 4,316,463 | A | | 2/1982 | Schmitz et al. | | |
| 4,559,042 | A | * | 12/1985 | Votel | ............................ | 604/192 |
| 4,723,937 | A | | 2/1988 | Sarnoff et al. | | |
| 4,874,388 | A | * | 10/1989 | Wong et al. | ................. | 604/891.1 |
| 5,019,046 | A | * | 5/1991 | Kohler | ........................ | 604/110 |
| 5,125,899 | A | | 6/1992 | Frignoli et al. | | |
| 5,709,668 | A | | 1/1998 | Wacks et al. | | |
| 6,022,339 | A | | 2/2000 | Fowles et al. | | |
| 6,045,534 | A | * | 4/2000 | Jacobsen et al. | .............. | 604/156 |
| 6,569,115 | B1 | * | 5/2003 | Barker et al. | ................. | 604/110 |
| 2007/0250004 | A1 | * | 10/2007 | Tung | ............................ | 604/110 |
| 2009/0299328 | A1 | | 12/2009 | Mudd et al. | | |

FOREIGN PATENT DOCUMENTS

GB    1284312 A    8/1972

* cited by examiner

*Primary Examiner* — Laura Bouchelle
*Assistant Examiner* — Melissa A Snyder
(74) *Attorney, Agent, or Firm* — Lucas & Mercanti, LLP

(57) ABSTRACT

The present invention relates to a security syringe comprising a hollow cylinder (1) with a pair of wings (11) and a tip (12), which houses: the injection mechanism (3), a piston (2), and an injection mechanism (3) with a needle (31), a spring (32) and a membrane (33). The piston (2) has a serrated crown in the lower part (21) thereof where a chamber seal exists (22) and breaks only with the interior point of the needle (31), having the ends of the piston (2) of an inferior disk (24) and a superior disk (25) that steadies the piston (2) inside the cylinder (1). Around the cylinder (1) there is a protective funnel (13) against accidental injections. The piston comprises a cap (26) which guarantees the hermeticity of the empty chamber.

7 Claims, 3 Drawing Sheets

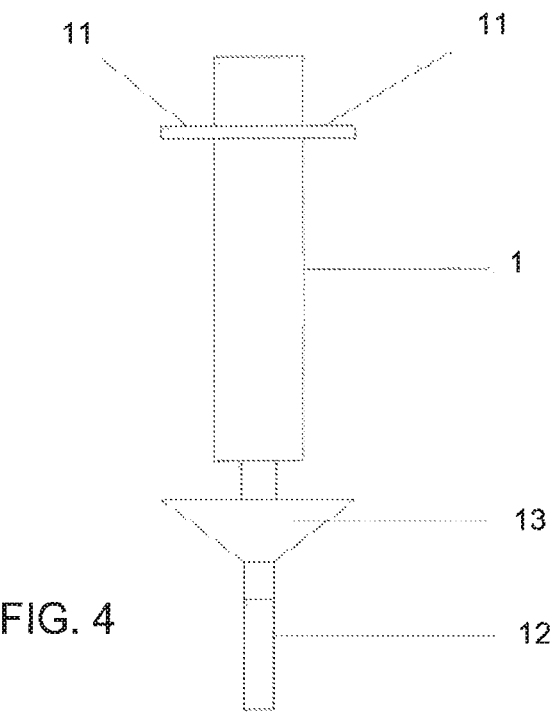
FIG. 2
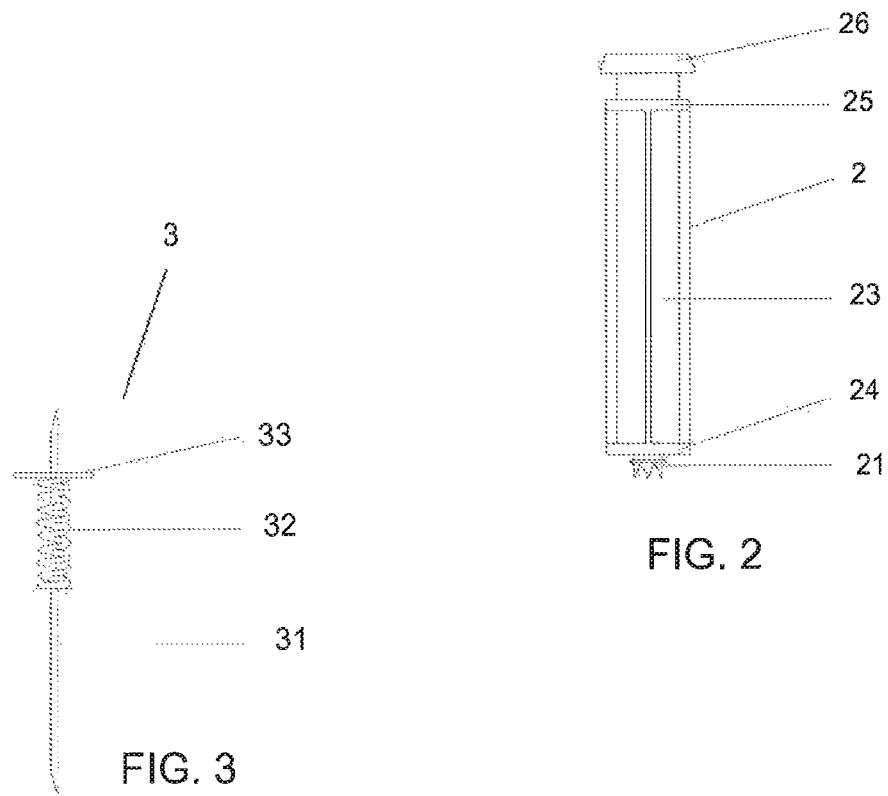
FIG. 3
FIG. 4

MEDICINAL BIOSECURITY AUTO DISPOSABLE SYRINGE

This application is a 371 of PCT/ES2010/070401 filed Jun. 16, 2010, which in turn claims the priority of ES U 200930368 filed Aug. 13, 2009, the priority of both applications is hereby claimed and both applications are incorporated by reference herein.

OBJECT OF THE INVENTION

The present invention consists of a security syringe that allows obtaining a safe injection system for the casual user, the health care staff, the patient and the entire environment, preventing the transmission when introducing the needle into the hood, in addition to a system of activation of the novel mechanism in opposition to the current state of the art.

BACKGROUND OF THE INVENTION

Currently there are syringes or needles used in the health centers which are not considered safe, because they do not have any system of protection that prevents the exposure of the health care and hygiene staff to the transmission of blood-borne diseases, and which can cause unwanted injections. Thus, the accidents of the health care staff produced by sharp objects mostly in hospitals and clinics are frequent, cases that are extremely worrying when it comes to serious infectious diseases such as Hepatitis B and C or HIV.

In addition, the high risk of suffering an injection when treating the patients generates personal stress on the health care staff in view of the possibility of being infected with an infectious disease. An accidental injection with a fluid infected by a virus can cause the medical leave, the temporary disability of the patient, even psychosis, until it is determined whether there has been infection, in addition to the high economic and legal burdens for the institutions.

Therefore it is necessary the creation and implementation of biosecurity material in ail these health centers and for the general population.

DESCRIPTION OF THE INVENTION

The invention being proposed consists of a high security syringe, comprising a cylinder that serves as a deposit of the injectable and facilitates the handling by the operator; a piston mounted on the interior of the cylinder and which slides in it, dragging the injectable towards the outside, guaranteeing full leakproofness; a mechanism composed of needle, spring and membrane and in addition a protective funnel.

Thus, the cylinder provides the basis for the displacement of the piston inside of it. Its main function is to serve as the reservoir for the injectable, as well as to aid in the handling. Said cylinder comprises a tip which is where the needle mechanism, spring and membrane are housed. The tip of the cylinder is a Luer hub, where any conventional needle can be coupled, such that this design can be used as a traditional disposable syringe. Near the upper part it has a pair of wings, which constitute the support for the operator and allow him to stabilize the cylinder in the hand.

The piston slides within the cylinder dragging the injectable towards the outside and guaranteeing full leakproofness. One of its key points is its sharp crown, which allows breaking the membrane to activate the mechanism at will. Once the needle mechanism has been activated it is housed in the receiving chamber. The seal chamber closes the lower part of the piston with a thin film that does not allow that the injectable enters the receiving chamber, and which breaks only with the interior point of the needle every time the mechanism is activated. The security inferior disk is in direct contact with the injectable dragging it and once it reaches the end of the path it is embedded in the bottom of the cylinder, thus avoiding pulling out the piston again, still another security measure. The security superior disk steadies the piston inside the cylinder and when it is pushed to the bottom of the cylinder it is secured in the extension, coadjuvating the inferior disk. Atop cap guarantees the hermeticity of the empty chamber.

The mechanism, as indicated above comprises a needle, similar to standard hypodermic, but without colored plastic barrel. On the needle the plastic membrane is injected. It also has a spring, the function of which is to be compressed and bear the load of the needle with the membrane, releasing its energy once the mechanism is activated. The membrane is made of plastic, for the case of semi-automatic mechanism activated at will, or is made of pharmaceutical gelatin or water soluble plastic for the fully automatic mechanism.

The syringe of the invention has a protective funnel, arranged in the lower part of the cylinder and around the tip, so that it protects the health care staff against accidental injections. It comprises the hood, which is the part of protection against accidental injection by keeping the needle in the protector, having inside of it the appropriate design to adapt to any Luer hub. It also has the protector, which is where the body of the needle is finally pressure-locked through the Luer universal system.

DESCRIPTION OF THE DRAWINGS

In order to complete the description being made and with the object of helping to a better understanding of the features of the invention, according to a preferred example of practical embodiment of the same, a set of drawings is accompanied as an integral part of said description wherein with an illustrative character and without limitation, the following has been represented:

FIG. 2. —shows a view of the piston (2) of the syringe of the invention.

FIG. 3. —shows a view of the injection mechanism (3), as well as the arrangement of its parts, membrane (33), needle (31) and spring (32).

FIG. 4. —shows a view of the cylinder (1) of the syringe of the invention.

PREFERRED EMBODIMENT OF THE INVENTION

Figure 1:
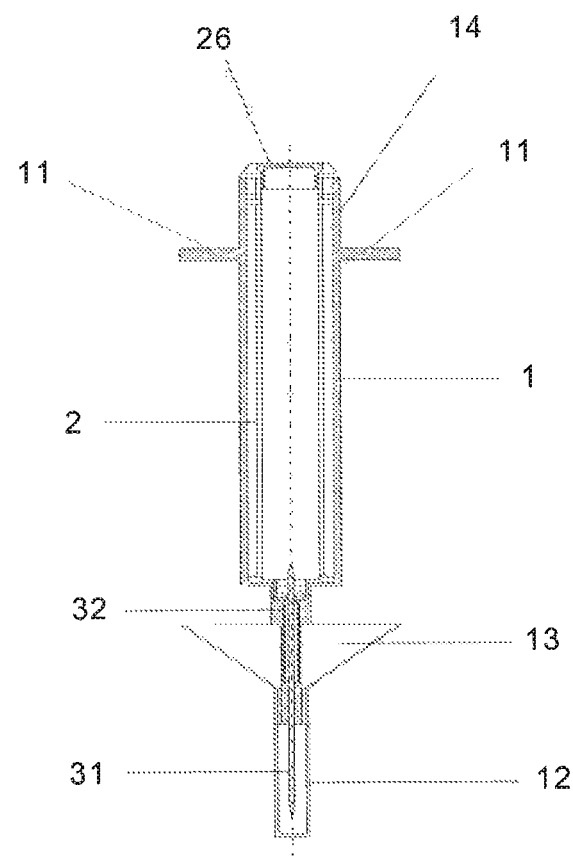
FIG. 1. —shows a sectional view of the syringe assembly of the invention.
Figure 5:
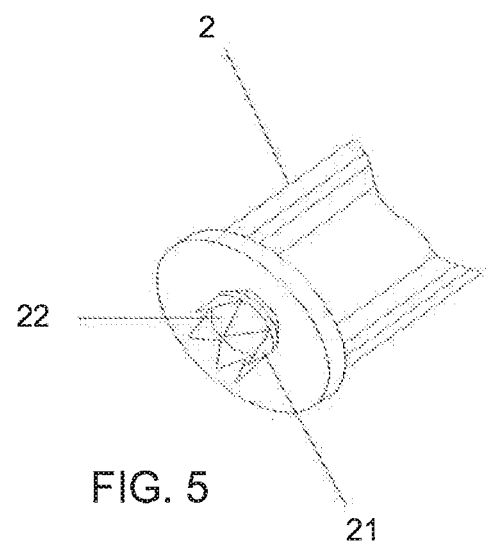
FIG. 5. —shows a detailed view of the lower part of the piston (2), where the arrangement of the chamber seal (22) can be observed.
Figure 6:
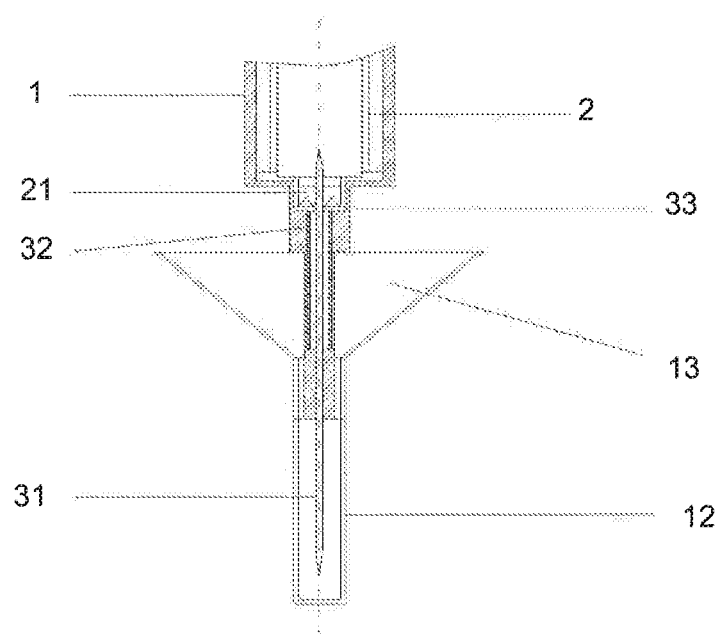
FIG. 6. —shows a detailed view of the lower part of the syringe assembly of the invention.

The present invention consists of a security syringe, comprising a cylinder (1), a piston (2) that slides in the interior of said cylinder (1), and an injection mechanism (3) and a protective funnel (13).

The hollow cylinder (1) serves as a deposit of the injectable and has a pair of wings (11) at the upper part. On these wings (11) there is the extension (14), which is the area where the piston (2) is secured, allowing said piston (2) to penetrate completely in the cylinder (1). At the lower part it has a tip (12) wherein the injection mechanism (3) is housed, and the tip of said cylinder (1) is designed to adapt to any standard Luer type-needle. The particularity of said cylinder (1) lies in that it has at the lower part, surrounding the injection mechanism (3), a protective funnel (13) against accidental injections, which consists of a hood designed to adapt to any syringe on the market, and the protector, where the body of the needle is finally pressure-locked.

The protective funnel (13) can be manufactured in plastic, water soluble plastic, latex, rubber, which may be alone or combined.

The piston (2) slides through the interior of the cylinder (1) dragging the injectable towards the outside and guaranteeing the leakproofness. At the lower part it has a serrated crown (21), in such a way that when pressing on the membrane (33) it breaks it and activates the mechanism, and there is a chamber seal (22) which is only broken with the interior point of the needle (31), every time that the mechanism is activated, and that prevents that the injectable enters the receiving chamber (23). In each of the ends of the piston (2) there is a protective disk (24, 25), where the inferior disc (24) drags the injectable and is embedded at the bottom of the cylinder (1), and the superior disk (25) which steadies the piston (2) within the cylinder (1). In addition the piston (2) has a cap (26) that guarantees the hermeticity of the empty chamber.

The injection mechanism (3) comprises a standard needle (31), a spring (32) and a membrane (33). The membrane (33) is made of plastic material for semi-automatic mechanism activated at will, and is made of pharmaceutical gelatin or water soluble plastic for automatic mechanism activated inadvertently, once the injectable has been used, achieving the programming of the activation time.

The invention claimed is:

1. A medicinal biosecurity auto disposable syringe, comprising:
   a hollow cylinder which deposits an injectable, the hollow cylinder having a pair of wings at an upper end and an injection mechanism at a tip, the tip at a lower end of the cylinder;
   a piston, which is movable and penetrates completely within the cylinder;
      the piston having a receiving chamber, a lower end and an upper end,
         the lower end having an inferior disk with a serrated crown and a chamber seal, the chamber seal preventing the injectable from entering the receiving chamber prior to the activation of an injection mechanism, and
         the upper end having a superior disk, the superior disk, which steadies the piston, is arranged inside the cylinder and is secured in the cylinder;
      the piston sliding through an interior of the hollow cylinder, pushing the injectable towards an outside and guaranteeing leakproofness,
   the tip being adaptable to accommodate a standard needle, and the injection mechanism having a standard needle, a spring, and a membrane;
   wherein when the piston fully pushes the injectable, then the inferior disk is embedded in the lower end of the cylinder and the serrated crown presses the membrane, the serrated crown breaks the membrane and activates the injection mechanism, wherein when the injection mechanism is activated, the chamber seal is broken with an interior point of the needle, and the injection mechanism is moved into the receiving chamber.

2. The Medicinal biosecurity auto disposable syringe, according to claim 1, further comprising a protective funnel around the tip of the cylinder to protect against accidental injections, the protective funnel has a hood, which adapts to any known syringe, and a protector, where a body of the needle is pressure-locked through Luer universal system.

3. The medicinal biosecurity auto disposable syringe according to claim 2, wherein the protective funnel can be manufactured from plastic material, water soluble plastic, latex, rubber, or combinations thereof.

4. The medicinal biosecurity auto disposable syringe according to claim 1, wherein the piston has a cap that guarantees hermeticity of an empty chamber.

5. The medicinal biosecurity auto disposable syringe according to claim 1, wherein the membrane is made of a plastic material.

6. The medicinal biosecurity auto disposable syringe according to claim 1, wherein the membrane is made of a pharmaceutical gelatin.

7. The medicinal biosecurity auto disposable syringe according to claim 1, wherein the membrane is made of a water-soluble plastic.

\* \* \* \* \*